United States Patent [19]

Su et al.

[11] Patent Number: 5,385,550
[45] Date of Patent: Jan. 31, 1995

[54] NEEDLE PROTECTIVE MEANS FOR PREVENTION AGAINST STAB AND VIRUS INFECTION

[76] Inventors: Chan-Ho Su; Yi-Hsien Su; I-Yan Su, all of No. 6, Alley 1, Lane 768, Pa Teh Road, Sec. 4, Taipei, Taiwan, Prov. of China

[21] Appl. No.: 219,258
[22] Filed: Mar. 29, 1994
[51] Int. Cl.6 .............................................. A61M 5/00
[52] U.S. Cl. .................................. 604/110; 604/192; 604/263
[58] Field of Search ............... 604/192, 198, 195, 187, 604/263, 110

[56] References Cited
U.S. PATENT DOCUMENTS

| | | | |
|---|---|---|---|
| 4,986,819 | 1/1991 | Sobel | 604/192 X |
| 4,994,041 | 2/1991 | Dombrowski et al. | 604/198 X |
| 4,998,922 | 3/1991 | Kuracina et al. | 604/263 X |
| 5,108,379 | 4/1992 | Dolgin et al. | 604/198 |
| 5,209,739 | 5/1993 | Talalay | 604/198 X |

Primary Examiner—John D. Yasko
Attorney, Agent, or Firm—Bacon & Thomas

[57] ABSTRACT

A needle protective means for prevention against stab and virus infection includes a front protector, a middle rubber sleeve, and a rear protector, being added to the conventional syringe, needle, and protective cap to ensure a used needle to be discarded not to unexpectedly harm any one. The front and the rear protectors fixedly receive the needle and the syringe, respectively, and the rubber sleeve binds and connects the front and the rear protectors together while it allows the front protector to be pulled forward to pass beyond the needle and thereby incases the same to prevent the point of the needle from stabbing others or spreading infectious virus.

9 Claims, 6 Drawing Sheets

FIG_6

NEEDLE PROTECTIVE MEANS FOR PREVENTION AGAINST STAB AND VIRUS INFECTION

BACKGROUND OF THE INVENTION

The present invention relates to a needle protective means for prevention against stab and virus infection, and more particularly to a needle protective means which includes a front protector, a middle rubber sleeve, and a rear protector being provided on and used together with the conventional syringe, needle, and needle cap to effect the safety both during the injection and after the disposal of discarded syringe and needle.

Nowadays, even with the increasingly advanced medical science and therapeutical technology, there are still so many types of virus causing diseases, such as cancers, AIDS, hepatitis-A, and hepatitis-B that can not be effectively prevented, controlled or cured. What is worse is that they might even be the products of modern technologies. Therefore, it is necessary to have adequate measures to prevent the occurence and spread of such diseases.

Hospitals are one of the places where various types of virus exist. One of the quickest and easiest way for people to get infected is the contact with medical apparatus. Particularly, the rate of injury or illness caused by stab of needle to medical persons or others is as high as more than 75%. This inevitably forms an occupational harm and reversely influences the work attitude of general medical personnel.

Figure 9:
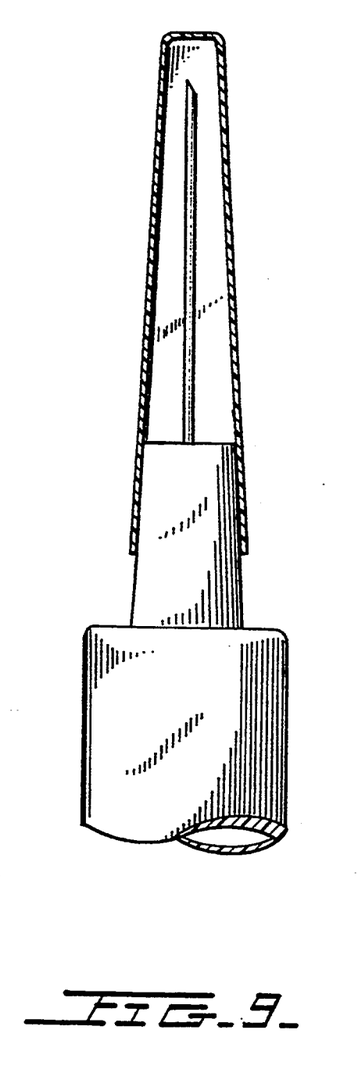
FIG. 9 illustrates a conventional needle attached to a syringe and protected with a cap.

FIG. 9 illustrates one of the most common ways to protect the needle of a conventional syringe, wherein a hard cap is used to cover the needle. The cap is removed before the injection and is then replaced to cover the needle before the latter is discarded, so that the probability of people being stabbed or infected by the disposed or discarded needles can be reduced. However, even in the course of replacing the protective cap to the needle, it is inevitable that the user is unexpectedly injured by the needle. In addition, since the conventional protective cap is separable from the needle and is therefore, easily lost. Under the circumstances, the conventional protective cap of needles can not effectively prevent the stab injury or infectious disease caused by needles during the course of use or disposal thereof.

SUMMARY OF THE INVENTION

It is therefore a primary object of the present invention to provide a needle protective means for prevention against stab and virus infection, including a front protector, a middle rubber sleeve, and a rear protector added to and between the conventional protective cap, needle, and syringe, such that, after the protective cap is removed and the needle is used, the front protector can be movably pulled upward and slightly inclined to wrap the entire needle therein, and thereby effectively secure the safety in wrapping the needle before the latter is discarded, as well as the safety in disposal of the discarded needles.

Another object of the present invention is to provide the above needle protective means for prevention against stab and virus infection, in which the front protector defines an chamber and has a needle passage formed at its top portion communicable with the chamber. An inward projection is formed at the intersection of the needle passage and the chamber such that an annular groove having a substantially reverse V-shaped cross section is formed around the inward projection for securely retaining a needle point therein without the risk of letting the needle pass through the needle passage of the front protector again.

A further object of the present invention is to provide the above needle protective means for prevention against stab and virus infection, in which the middle rubber sleeve is disposed between the front and the rear protectors to wrap their joint and connect them together. The rubber sleeve has an upper and a lower rims having larger diameter than the remaining part thereof for fitly and tightly engaging into the externally formed annular grooves of the front and the rear protectors, respectively. If necessary, the external annular grooves can also be formed at other suitable position on the front and the rear protectors.

A still further object of the present invention is to provide the above needle protective means for prevention against stab and virus infection, in which the middle rubber sleeve can be replaced with a plurality of rubber rings while the front and the rear protectors are provided with two or more laterally extended grooved wings at their adjoining edges, so that the rubber rings are put over and engaged into two vertically corresponding grooved wings and thereby firmly bind the front and rear protector together.

BRIEF DESCRIPTION OF THE INVENTION

The present invention can be best understood by referring to the following detailed description of the preferred embodiments and the accompanying drawings, wherein.

DETAILED DESCRIPTION OF THE PREFERRED EMBODIMENTS

Figure 1:
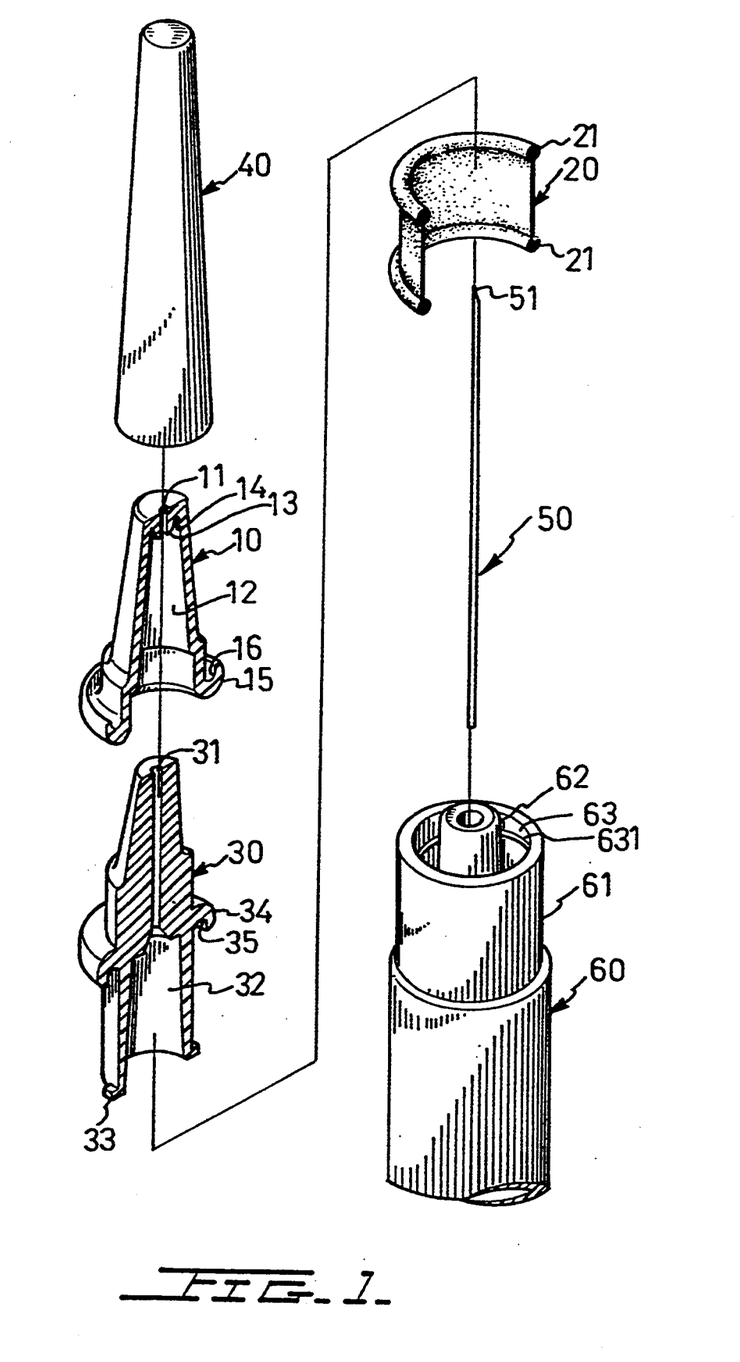
FIG. 1 is an exploded perspective of a first embodiment of the present invention, wherein a part of the front and the rear protectors are cut away to better show the structure thereof.
Figure 5:
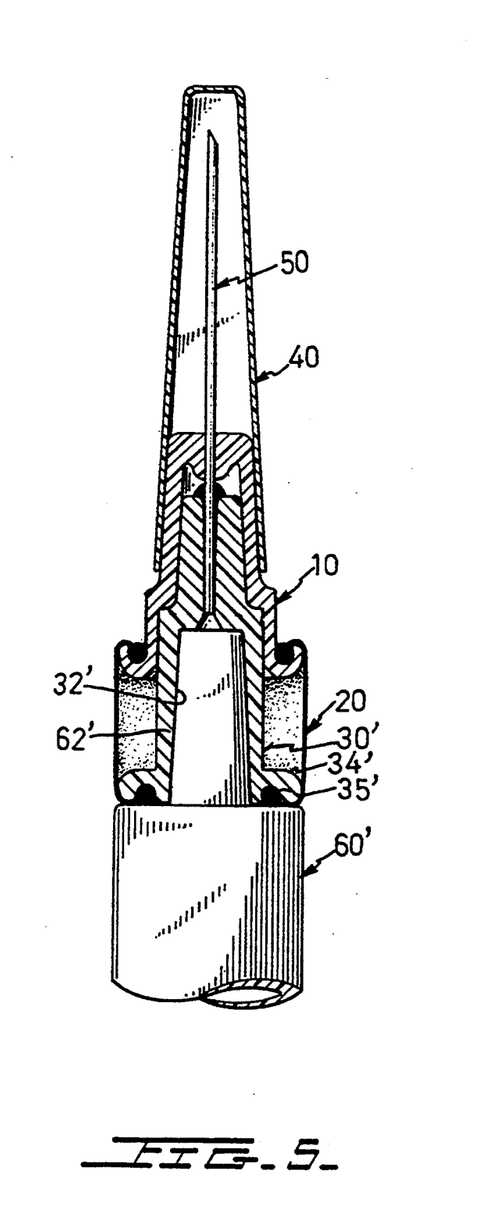
FIG. 5 is an assembled vertical sectional view showing a second embodiment of the present invention.
Figure 6:
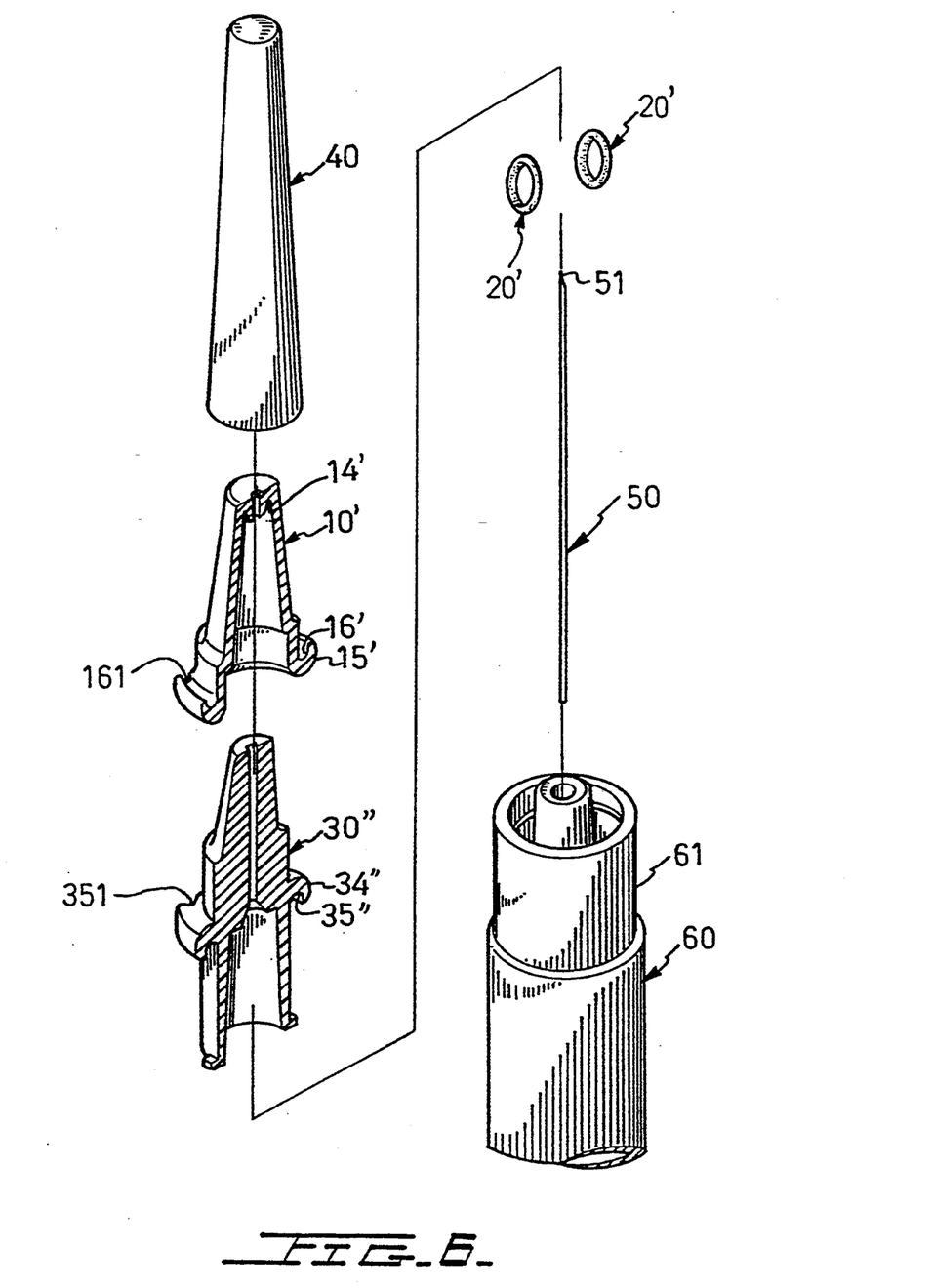
FIG. 6 is an exploded perspective of a third embodiment of the present invention.

As shown in FIGS. 1, 5, and 6, the present invention is a protective means added to a commonly used syringe 60 or 60' to prevent the point 51 of a used needle 50 thereof from exposure and unexpectedly injuring a person or causing infectious disease to others.

The present invention includes a front protector 10, a middle rubber sleeve 20, and a rear protector 30 disposed between a conventional needle cap 40 and a syringe 60 or 60' to hold a conventional needle 50 therein.

Figure 2:
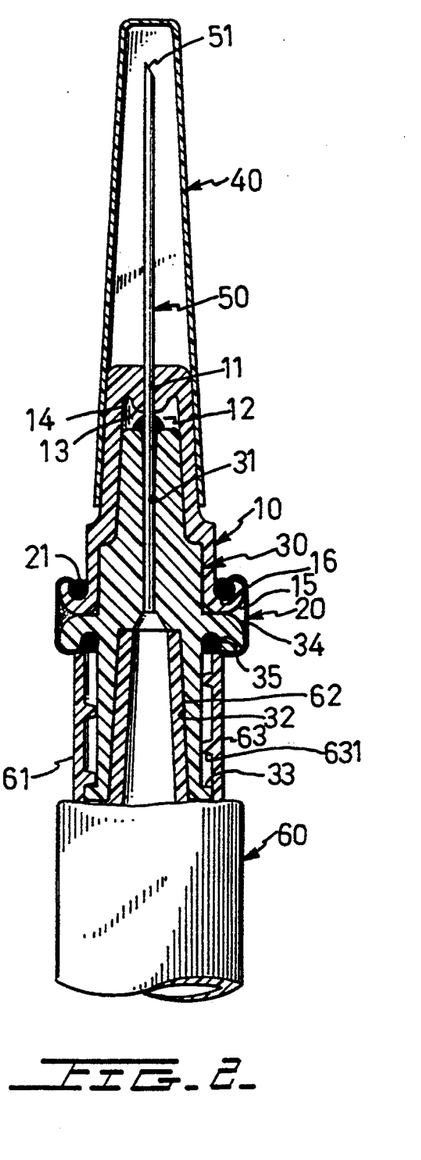
FIG. 2 is an assembled vertical sectional view of FIG. 1 showing the present invention before use.

Please refer to FIGS. 1 and 2. The front protector 10 is substantially a conic member having a bottom portion tapering off to a smaller top portion and thereby defines a hollow chamber 12 therein. The top portion of the front protector 10 has a centered needle passage 11 extended in the direction of the longitudinal axis of the conic protector 10 and communicable with the chamber 12. An inward projection 13 projecting from the top portion of the front protector 10 into the chamber 12 such that an annular groove 14 having a substantially reverse V-shaped cross profile is formed around the projection 13. The needle passage 11 extends through the projection 13 and communicates with the chamber 12 at the lowest point of the projection 13. The front protector 10 has a flange 15 formed at its lower outer periphery. The flange 15 first extends outward and then upward such that an annular groove 16 is formed between the lower portion and the flange 15 of the front protector 10. The flange 15 has smooth and round periphery.

The middle rubber sleeve 20 can be made of rubber, resin, or any other ductile material and has two rims 21 which have much larger thickness than that of the remaining parts of the rubber sleeve 20 and function like two lashing rings. The lashing rings 21 have a profile suitable for fitly engaging into the annular groove 16 of the front protector 10 and another annular groove 35 formed on the rear protector 30 which will be described in more details as follows. It is preferable for the rubber sleeve 20 to have a total extended length about one half of the length of the needle 50.

The rear protector 30 has an upper portion which has an outer configuration substantially corresponding to an inner configuration of the chamber 12 of the front protector 10, and a lower portion defining a hollow chamber 32 therein. A needle passage 31 extends through full length of the upper portion to communicate with the chamber 32 at a lower end and to align with the needle passage 11 of the front protector 10 at an upper end. Two raidially and outwardly extended lugs 33 oppositely positioned at a lower outer periphery of the lower portion. A flange 34 radially extends outward from a middle or waist portion of the rear protector 30 and then turns downward to form an annular groove 35 between the flange 34 and an outer wall surface of the lower portion of the rear protector 30. The flange 34 has smooth and round periphery.

The three elements of the present invention, i.e. the front protector 10, the middle rubber sleeve 20, and the rear protector 30, can be attached to the conventional syringe 60 or 60', needle 50, and then be covered by the conventional protective cap 40 through automated manufacturing process by, first, inserting the needle 50 through the chamber 32 and the needle passage 31 of the upper portion of the rear protector 30 with the point 51 of the needle 50 fully projecting out of the rear protector 30, then, put the front protector 10 over the projected needle 50 and the upper portion of the rear protector 30 so that the latter is fitly received in the chamber 12, and, finally, put the rubber sleeve 20 over the mutually engaged front and rear protector 10, 30 with the two rims or lashing rings 21 fitly falling into the annular grooves 16, 35, respectively, so that the flanges 15, 34 are wrapped within and bound together by the rubber sleeve 20.

The syringe 60 has a hollow head portion 61 inside which a forward projected frustum 62 is provided to connect and communicate with the needle 50 and internal threads 631 are provided on an inner wall surface 63 of the head portion 61. The frustum 62 has an outer profile just for it to he fitly received inside the chamber 32 defined by the lower portion of the rear protector 30. The two lugs 33 at the lower outer periphery of the rear protector 30 permit the rear protector 30 to move along the internal threads 631 and be fixedly screwed inside the syringe 60. With this arrangement, the syringe 60, the rear protector 30, and the needle 50 together provide a continued through passage for the injection contained inside the syringe to smoothly flow the needle 50 and be injected through the point 51.

Figure 3:
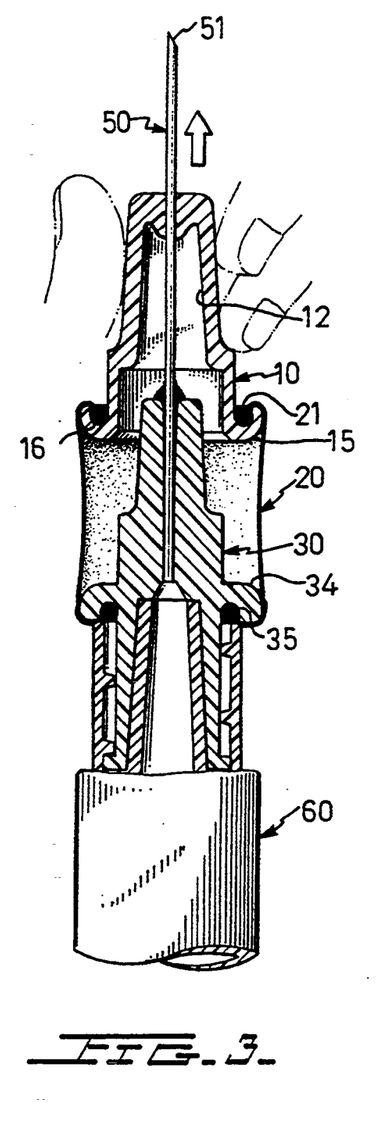
FIG. 3 is an assembled vertical sectional view similar to FIG. 2 showing the present invention in use.
Figure 4:
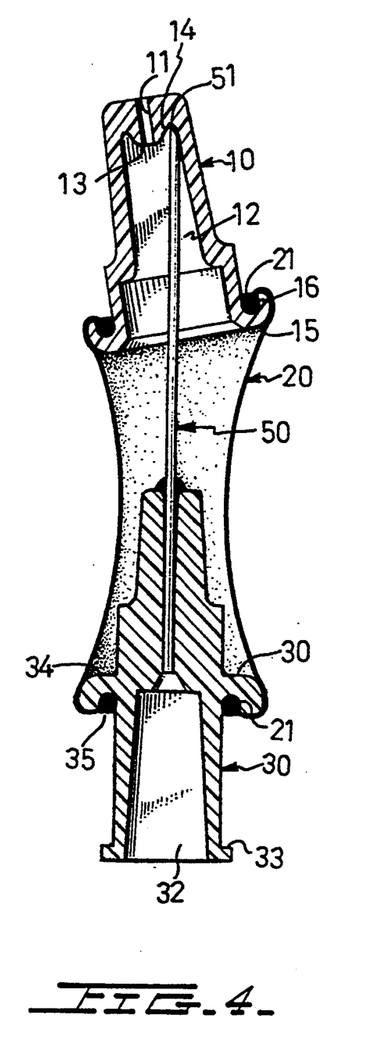
FIG. 4 is a vertical sectional view showing the present invention in a final state after use.

Please now refer to FIGS. 2, 3, and 4. When the syringe 60 with the present invention is used in injection, the protective cap 40 is removed from the needle 50 and the front protector 10 to expose the point 51. After the injection, the front protector 10 is pulled toward the point 51. At this point, the ductile rubber sleeve 20 surrounding and wrapping the flanges 15, 34 and retained by the annular grooves 16, 35 is accordingly pulled, extended, and deformed, allowing the front protector 10 to be moved forward until the same passes beyond the point 51 and the point 51 disengages from the needle passage 11 and becomes completely incased by the front protector 10. At this point, the front protector 10 is slightly inclined and released, and the point 51 shall fall into the reverse V-shaped annular groove 14 and be limited therein. With the elasticity of material, the rubber sleeve 20 keeps the front protector 10 in place to press against and cover the needle 50 without the risk of exposing the point 51 and therefore unexpectedly harming anyone. Then, the rear protector 30 is rotated to allow the lugs 33 to separate from the internal threads 631 and accordingly, the syringe 60, so that the needle 50 is discarded when it is securely incased by the front protector 10, rubber sleeve 20, and the rear protector 30.

FIG. 5 illustrates a second embodiment of the present invention to match with another type of syringe 60' having a different head portion 61' that is also commonly used nowadays. The head portion 61' of the syringe 60' consists of one single frustum 62'. This second embodiment of the present invention consists of the same front protector 10 and rubber sleeve 20, but a differently designed rear protector 30'. The rear protector 30' is substantially the same as the upper portion of the rear protector 30 and defines a chamber 32' which just fitly and tightly receives the frustum 62' therein. The lower portion of the rear protector 30 is removed from the rear protector 30' while flange 34' and an annular groove 35' similar to the flange 34 and the annular groove 35 are provided at the bottom outer periphery of the rear protector 30'. All the other parts and structure of the rear protector 30' are the same as those of the rear protector 30. The operation and the function of the second embodiment of the present invention is exactly the same as the first one.

The annular grooves 16, 35, 35' of the present invention can also be provided at other suitable positions on the flanges 15, 34, 34' to meet different manufacturing processes.

Figure 7:
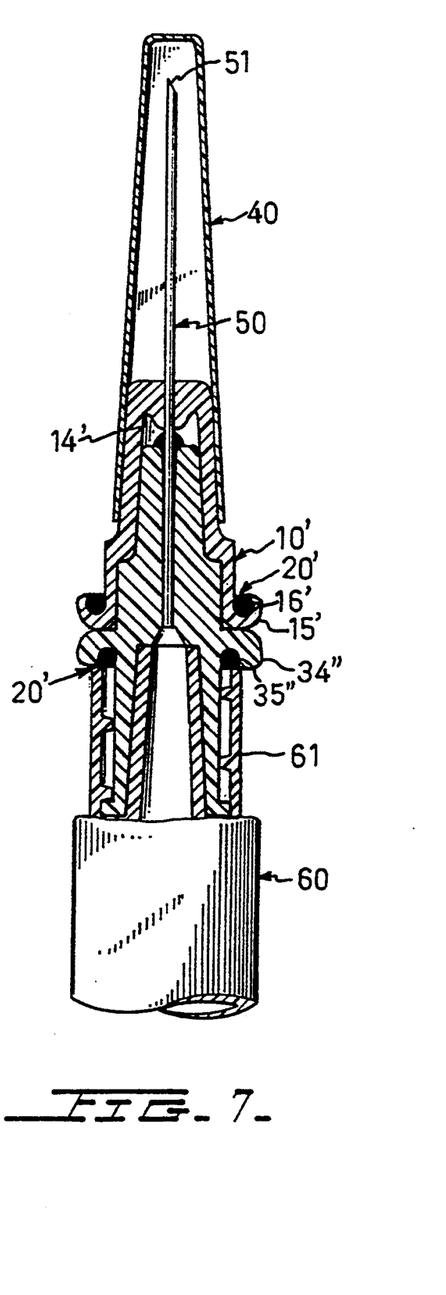
FIG. 7 is an assembled vertical sectional view of FIG. 6 showing the present invention in a state before use.

FIG. 6 illustrates a third embodiment of the present invention which consists of a front protector 10', a plurality of rubber rings 20', and a rear protector 30''. The front protector 10' is similar to the front protector 10 except that it includes two or more mutually spaced wings 15' at its lower outer periphery instead of a continuous flange. The wings 15' have a structure and cross section similar to that of the flange 15 to form grooves 16' between the wings 15' and the outer periphery of the front protector 10'. The rear protector 30" is similar to the rear protector 30 except that it includes two or more mutually spaced wings 34" corresponding to the wings 15' of the front protector 10'. The wings 34" have a structure and cross section similar to that of the flange 34 to form grooves 35" between the wings 34" and the outer wall surface of the rear protector 30". The rubber rings 20' are separately put over the corresponding wings 15' and 34" and fall into the corresponding grooves 16' and 35", as shown in FIG. 7, so that the front and the rear protector 10', 30" are bound together by the rubber rings 20'. Dents 161, 351 can be further formed at two ends of the grooves 16", 35", respectively, for the rubber rings 20' to engage into and thereby further secures the firm binding of the front and the rear protectors 10', 30".

Figure 8:
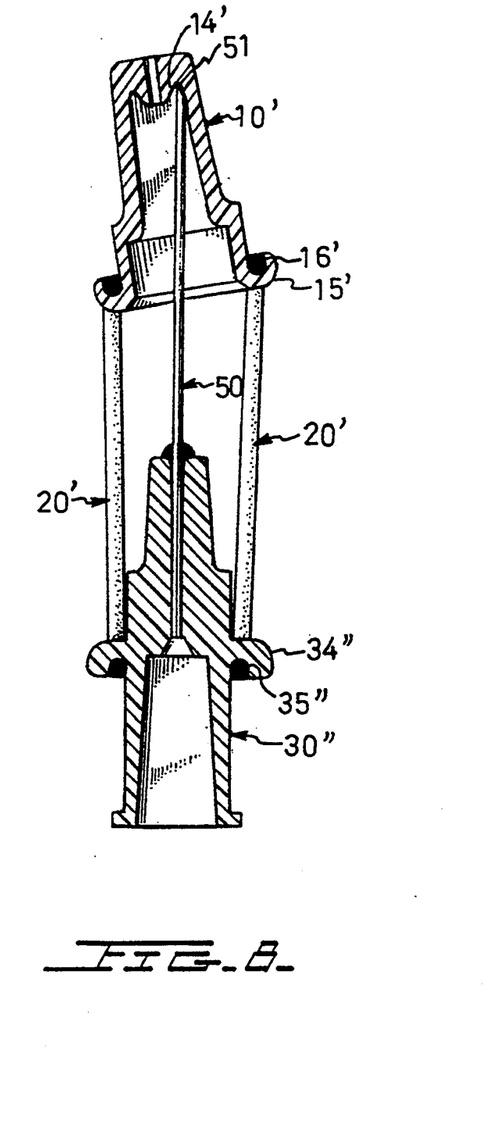
FIG. 8 is an assembled vertical sectional view of FIG. 6 showing the present invention in a final state after use.

After a syringe 60 and needle 50 are used, pull the front protector 10' forward to separate from the rear protector 30" but still distantly connected with the latter by the rubber rings 20' until the front protector 10' passes beyond the needle point 51. Then, slightly incline the front protector 10', allowing the point 51 to fall into a reverse V-shaped annular groove 14' similarly formed as the annular groove 14 and be retained therein for disposal, as shown in FIG. 8.

What is claimed is:

1. A needle protective means for prevention against stab and virus infection being used together with a conventional syringe, needle, and protective cap, comprising a front protector, a middle rubber sleeve, and a rear protector;

said front protector defining a first chamber therein and having an inward projection formed at a top portion thereof to project into said first chamber and thereby forming a first annular groove between said front protector and said inward projection, said front protector further having a first needle passage extending through said top portion and said inward projection of said front protector to communicate with said first chamber, and a flange radially outward and then upward extending from a lower outer periphery of said front protector to form a second annular groove between said first flange and said lower outer periphery of said front protector;

said middle rubber sleeve being made of ductile material and having two rims which are expanded to have larger thickness than that of the remaining part of said rubber sleeve and thereby functioning as two lashing rings;

said rear protector consisting of an upper portion and a lower portion, said upper portion being suitable for fitly engaging into said first chamber, said lower portion defining a second chamber which communicates with a second needle passage extending through said upper portion, said rear protector further having a second flange radially outward and then downward extending from a middle or waist portion of said rear protector to form a third annular groove between said second flange and said middle portion of said rear protector, and two lugs radially outward extending from a lower outer periphery of said rear protector;

said middle rubber sleeve being put over said first and said second flanges with said thicker rims falling into said second and said third annular grooves such that said first and said second flanges are closely wrapped and bound together;

said first and said second needle passages aligning with each other after said rear protector having been received in said first chamber of said front protector to allow said needle to extend therethrough and finally project out of said front protector;

said syringe having a head portion consisting of a needle support and an outer wall, on an inner surface of which internal threads being provided so that said rear protector can be firmly but detachably screwed to said syringe by the engagement of said lugs of said rear protector with said internal threads; and said front protector being capable of being pulling forward to separate from said rear protector but still connecting said rear protector by means of said rubber sleeve which is extended and deformed under pull force, said front protector, when being pulled to completely pass beyond said needle and be slightly inclined, together with said extended rubber sleeve and said rear protector incasing said needle with a point of said needle pressing against said first annular groove of said front protector.

2. A needle protective means for prevention against stab and virus infection as claimed in claim 1, wherein said rear protector has shortened length by removing said lower portion from said rear protector and said second chamber is directly defined by said upper portion of said rear protector to receive said needle support of said syringe and firmly connects said rear protector to said syringe.

3. A needle protective means for prevention against stab and virus infection as claimed in any one of claims 1 or 2, wherein said first annular groove between said inward projection and said front protector has a reverse V-shaped cross section.

4. A needle protective means for prevention against stab and virus infection as claimed in any one of claims 1 or 2, wherein said middle rubber sleeve has a total extended length preferably about one hale of the length of said needle.

5. A needle protective means for prevention against stab and virus infection as claimed in any one of claims 1 or 2, wherein said front, said rear protectors, said first chamber and said second chamber have a substantially conic profile having a wider lower portion which tapers off to a narrow top portion, and said first and said second flanges having smooth and round periphery.

6. A needle protective means for prevention against stab and virus infection as claimed in any one of claims 1 or 2, wherein said second and said third annular grooves can also be formed at a lower or a lateral position of said first and said second flanges, respectively.

7. A needle protective means for prevention against stab and virus infection as claimed in any one of claims 1 or 2, wherein a plurality of rubber rings are used to replace said rubber sleeve, two or more mutually spaced and grooved first and second wings on said front and said rear protectors, respectively, are designed to replace said first and said second flanges and said second and said third annular grooves but have the same structure and cross section as said first and said second flanges, and said rubber rings being put over every two of said first and said second wings correspondingly located on said front and said rear protectors, respectively, to bind them together.

8. A needle protective means for prevention against stab and virus infection as claimed in claim 7, wherein each of said grooved first and second wings has dents formed at two ends thereof to secure the engagement of said rubber rings with said grooved wings.

9. A needle protective means for prevention against stab and virus infection as claimed in claim 3, wherein a plurality of rubber rings are used to replace said rubber sleeve, two or more mutually spaced and grooved first and second wings on said front and said rear protectors, respectively, are designed to replace said first and said second flanges and said second and said third annular grooves but have the same structure and cross section as said first and said second flanges, and said rubber rings being put over every two of said first and said second wings correspondingly located on said front and said rear protectors, respectively, to bind them together.

* * * * *